United States Patent [19]
Goralski et al.

[11] Patent Number: 4,886,924
[45] Date of Patent: Dec. 12, 1989

[54] STEREOSPECIFIC SYNTHESIS OF [E]-ALKENES FROM ENAMINES VIA HYDROBORATION

[75] Inventors: Christian T. Goralski, Midland, Mich.; Bakthan Singaram; Herbert C. Brown, both of West Lafayette, Ind.

[73] Assignee: The Dow Chemical Company, Midland, Mich.

[21] Appl. No.: 258,743

[22] Filed: Oct. 17, 1988

[51] Int. Cl.$^4$ .............................................. C07C 1/32
[52] U.S. Cl. .................................... 585/318; 585/328; 585/357; 585/638
[58] Field of Search ................ 585/318, 328, 357, 638

[56] References Cited
PUBLICATIONS

Christian T. Goralski et al., "Stereospecific Synthesis of Pure [Z]-and [E]-Alkenes from Enamines via Hydroboration," presented to National American Chemical Society Meeting, Toronto, Canada (Jun. 1988).
Christian T. Goralski et al., "Hydroboration. 81. Synthesis of 2-(Dialkylamino)boronic Esters and Acids via Hydroboration of Enamines. A Convenient Preparation of β-Dialkylamino Alcohols," The Journal of Organic Chemistry, vol. 52, 1987, pp. 4014–4019.
J. W. Lewis et al., "Hydrogenolysis of Enamines. Part II. Hydroboration-Protonolysis," J. Chem. Soc. (B) Phys. Org., 1969, pp. 863–867.
J. W. Lewis et al., "Alkenes from Enamines via Hydroboration," Tetrahedron Letters No. 30, 1964, pp. 2039–2042.
Daniel J. Pasto et al., "Transfer Reactions Involving Boron. IX. Mechanism of Product Formation in the Hydroboration of Vinyl Halides," J. Org. Chem., vol. 31, Sep. 1966, pp. 2773–2777.
Daniel J. Pasto et al., "Transfer Reactions Involving Boron. X. The Stereochemistry of Eliminations Involving β-Substituted Organoboranes," J. Org. Chem., vol. 31, Sep. 1966, pp. 2777–2784.
Gerald L. Larson et al., "A Synthesis of Olefins via Hydroboration of Cyclic Trimethylsilyl Enol Ethers," Tetrahedron Letters No. 46, 1975, pp. 4005–4008.
Gilbert Stork et al., "The Enamine Alkylation and Acylation of Carbonyl Compounds," The Journal of the American Chemical Society, vol. 85, Jan. 20, 1963, pp. 207–222.

Primary Examiner—Curtis R. Davis
Attorney, Agent, or Firm—Paula Sanders Ruhr

[57] ABSTRACT

A process for the stereospecific synthesis of [E] alkenes from enamines comprising the steps of hydroborating the enamine; esterifying the organoborane so formed and oxidizing the boronic ester in the presence of hydrogen peroxide and in the absence of added base under conditions sufficient to form the [E] alkene in high yield.

11 Claims, No Drawings

STEREOSPECIFIC SYNTHESIS OF [E]-ALKENES FROM ENAMINES VIA HYDROBORATION

BACKGROUND OF THE INVENTION

The current invention relates to the synthesis of unsaturated hydrocarbyl compounds such as alkenes from enamines via hydroboration. The invention particularly relates to the stereospecific formation of the [E] isomers of such compounds.

Lewis et al., *J. Chem. Soc.* (B), 1969, 863 teach that enamines prepared from ketones can be subjected to hydroboration followed by hydrolysis in acetic acid to the corresponding aminoboronic acid which upon heating undergoes elimination to produce the corresponding alkenes. Borane is taught to be useful as the hydroborating agent and generally the hydroboration is conducted at reduced temperatures.

Larson et al., *Tetrahedron Letters*, 1975, 4005 discuss the synthesis of alkenes via the hydroboration of cyclic trimethylsilyl enol ethers. The stereospecific synthesis of unsymmetrical cyclic alkenes is taught to be possible when single isomers of the trimethylsilyl enol ethers are available as starting materials.

The existing methods for the preparation of alkenes are not without problems such as the necessity of harsh reaction conditions and the inability to obtain high yields of specific stereoisomers. Thus, what is needed is a simple process for the preparation of alkenes that operates under mild conditions and that has utility for the preparation of stereospecific isomers in high yields.

SUMMARY OF THE INVENTION

The present invention is such a process for preparing [E] or trans isomers of alkenes from enamines comprising the three essential steps of
(1) reacting an enamine wherein the enamine has an alkene portion corresponding to an alkene selected from the group consisting of $C_{3-100}$ linear alkenes and $C_{12-100}$ cyclic alkenes with a hydroborating agent under conditions sufficient to form an organoborane;
(2) contacting the organoborane formed in step (1) with an esterifying agent under conditions sufficient to form a boronic ester; and
(3) oxidizing the boronic ester formed in step (2) in the presence of hydrogen peroxide and in the absence of added base,
under reaction conditions sufficient to form the [E] isomer of the alkene corresponding to the alkenyl portion of the starting enamine.

It is surprising that the process of this invention results in a high yield of trans or [E] isomers rather than in the formation of a mixture of isomers.

The [E] isomers of the alkenes formed by the process of this invention have a wide variety of uses. For example, they may be used as starting materials for more complex organic molecules or as monomers in the preparation of polymers.

DETAILED DESCRIPTION OF THE INVENTION

The enamine starting materials useful in the practice of this invention are alkenyl amines wherein an amine nitrogen and an alkenyl carbon are covalently bonded. It is preferred that the isomer of the enamine wherein the alkene portion has the [E] configuration is used. In the enamine, the [E] configuration corresponds to the following

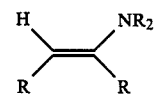

FIG. 1 wherein R represents a hydrocarbyl group or groups.

The enamines may, in some cases, be obtained commercially or may be prepared by the reaction of a secondary amine and a carbonyl compound. Carbonyl compounds useful in the preparation of enamines used in the practice of this invention include acyclic ketones, cyclic ketones having more than 12 carbon atoms in the cyclic structure, arylalkyl ketones, substituted arylalkyl ketones and heteroaryl alkyl ketones. The carbonyl compounds may be unsubstituted or may contain inert substituents. For purposes of this invention, inert substituents are those which will not interfere with the formation of the enamines, the hydroboration of the enamines so formed, the esterification of the organoboranes or the subsequent oxidation reactions to form alkenes. Examples of suitable inert substituents include alkyl, aryl, substituted aryl and heteroaryl such as pyridine and thiophene. The carbonyl compounds useful in the preparation of enamines useful in the practice of this invention contain at least about 3 carbon atoms in the case of acyclic carbonyl compounds and at least about 12 carbon atoms in the case of cyclic carbonyl compounds and no more than about 100 carbon atoms.

Non-limiting examples of carbonyl compounds useful in the preparation of enamines used in the practice of this invention include propiophenone, butyrophenone and other aryl alkyl ketones, phenyl benzyl ketone, 2-propionylthiophene and 4-propionylpyridine.

The carbonyl compounds are reacted with amines to prepare the enamines which undergo hydroboration in the practice of this invention. Secondary amines are useful for this purpose. The secondary amines useful in the preparation of the enamines may be cyclic, acyclic and may be substituted or unsubstituted. Non-limiting examples of useful secondary amines include pyrrolidine, piperidine, hexamethyleneimine, morpholine and benzylmethylamine.

The enamines are prepared by methods known in the art such as the method described by Stork et al., *J. A. C. S.*, 1969, 102 which is herein incorporated by reference. Generally, enamines are prepared by the reaction of an aldehyde or ketone with a secondary amine in the presence of a dehydrating agent such as anhydrous potassium carbonate. Under these conditions, the ketones are converted directly into their enamines. Aldehydes are generally changed into the nitrogen analog of an acetal which then decomposes on distillation to form the enamines and a secondary amine.

Hydroborating agents useful in the process of this invention include borane and diborane. For ease of handling, it is preferred to use a borane complex such as borane.dimethyl sulfide, borane.tetrahydrofuran or borane.1,4-oxathiane. When diborane is used, it is preferred to use it in a di-lower alkyl ether. Preferred examples of useful hydroborating agents include borane.dimethyl sulfide and borane.tetrahydrofuran.

The hydroboration reaction in the practice of this invention is conducted under mild conditions. Temperatures useful in the practice of this invention are any under which the reaction will occur. Preferably temperatures are at least about −20° C. and no greater than about 25° C. It is more preferred to conduct the hydroboration at about 25° C. Pressures useful in the practice of this invention are any under which the reaction will proceed and may include subatmospheric or superatmospheric. It is preferred to conduct the hydroboration reaction at about atmospheric pressure for the sake of convenience.

The enamine and hydroborating agent may be mixed in any relative amounts which will permit the reaction to proceed. Preferably the molar ratio of enamine to hydroborating agent is at least about 1.0:1.0 and no greater than about 2.0:1.0. It is more preferred that the ratio is at least about 1.0:1.1 and no greater than about 1.1:1.0.

The enamine and hydroborating agent are advantageously contacted in the presence of a solvent. Such solvents may include di-lower alkyl ethers such as dimethyl ether, diethyl ether, dipropyl ether; diethylene glycol dimethyl ether; or tetrahydrofuran. A preferred solvent is tetrahydrofuran (THF).

The hydroboration reaction is allowed to proceed until at least about 75 mole percent of the enamine is converted to an organoborane. It is preferred that at least about 90 mole percent of the enamine is converted to an organoborane and more preferred that at least about 98 mole percent is converted. It is preferred that the reaction proceed at least about one hour. It is also preferred that the reaction proceed no longer than about 24 hours and more preferred that it proceed no longer than about 12 hours. It is most preferred that the reaction proceed no more than about 6 hours. Thus, most preferred reaction times range from at least about one hour to no more than about 6 hours.

The organoborane prepared as described above is esterified followed by oxidation to form the trans alkene. Esterifying agents useful in the process of this invention include lower alkanols and lower alkyl diols wherein lower alkyl means alkyl groups having from 1 to about 6 carbon atoms. Non-limiting examples of useful esterifying agents include methanol, ethanol, propanol, butanol, pentanol, ethylene glycol and 1,3-propanediol.

The esterification reaction in the practice of this invention is conducted under mild conditions. Temperatures useful in the esterification step are any under which esterification will occur. Preferably temperatures are at least about 0° C. and no greater than about 70° C. It is more preferred to conduct the esterification at about 25° C. Pressures useful in the practice of this invention are any under which the reaction will proceed and may include subatmospheric or superatmospheric pressures. It is preferred to conduct the esterification reaction at about atmospheric pressure.

The organoborane and esterification agent may be mixed in any relative amounts which will permit the reaction to proceed. Preferably the molar ratio of organoborane to esterification agent is at least about 2:1 and no greater than about 2.2:1.0. It is more preferred that the ratio is about 2.1:1.0 to 2.0:1.0.

The esterification is advantageously conducted in the presence of a solvent. For the sake of convenience, it is preferred to use the solvent used in the hydroborating step although other solvents may be used.

The esterification reaction is allowed to proceed until at least about 75 mole percent, more preferably at least about 90 mole percent and most preferably at least about 95 mole percent of the organoborane is converted to a boronic ester. It is preferred that the reaction proceed at least about one hour. It is also preferred that the reaction proceed no longer than about 6 hours and more preferred that it proceed no longer than about 4 hours. It is most preferred that the reaction proceed no longer than about 2 hours. Thus, most preferred reaction times range from at least about one hour to no more than about 2 hours.

The ester so formed is then oxidized to form the desired [E] isomer of the alkene corresponding to the alkene portion of the enamine starting material. The ester is oxidized in the presence of hydrogen peroxide and in the absence of any added base. The oxidation reaction is exothermic and it is preferred to cool the reaction, e.g., by using a water bath, so that the temperature is maintained at or below about 30° C.

The [E] alkene is formed in this step essentially to the exclusion of the [Z] isomer. Stereochemical purity of greater than 99 percent is preferably obtained. The yield of the desired [E] alkene is the percentage of the starting enamine which is converted to the [E] alkene. It is preferred that the yield is at least about 65 percent and more preferred that it is at least about 70 percent based on the starting enamine.

ILLUSTRATIVE EMBODIMENTS

The following examples are given to illustrate the invention and should not be interpreted as limiting it in any way. Unless stated otherwise, all parts and percentages are given by weight.

EXAMPLE 1

Preparation of [E]-1-Phenyl-1-Propene

To a 20 ml, 20 mmole portion of a 1.0M solution of [E]-1-morpholino-1-phenyl-1-propene in tetrahydrofuran (THF), a 2.0 ml, 20 mmole portion of 10.0M borane.dimethyl sulfide complex is added with stirring. The mixture is stirred for one hour. A yellow color forms immediately and fades completely within the first 0.25 hour. The absence of the borane.dimethyl sulfide complex is confirmed by $^{11}B$ NMR spectroscopy.

Two ml of methanol are added and the solvent is evaporated at 25° C. under 20 Torr of pressure. The resulting boronic ester is dissolved in THF to provide a 1.0M solution. It is oxidized using 2.3 ml 30% hydrogen peroxide at 25° C. The exothermic reaction is controlled by the rate of addition of the hydrogen peroxide and by water bath cooling to maintain temperature below 30° C. Water (20 ml) and pentane (100 ml) is added to the reaction mixture. The organic phase is quickly washed with 3N HCl (2×10 ml), water (2×10 ml), and dried over anhydrous $MgSO_4$. Solvent is evaporated and the residue is purified by distillation to give 1.7 g of pure [E]-1-phenyl-1-propene in a yield of 73 percent. The boiling point is 72°–74° C. at 20 Torr. The stereochemical purity is found to be greater than 99 percent by $^1H$ and $^{13}C$ NMR spectroscopy and by capillary GC analysis.

EXAMPLE 2

Preparation of [E]-1-(2-Thienyl)-1-Propene

The procedure is repeated using [E]-1-morpholino-1-(2-thienyl)-1-propene as a starting material. A 1.9-g portion of [E]-1-(2-thienyl)-1-propene is prepared indicating a yield of 77 percent. The stereochemical purity is found to be greater than 99 percent by $^1H$ and $^{13}C$ NMR spectroscopy.

EXAMPLE 3

Preparation of [E]-1,2-Diphenylethene

The procedure described in Example 1 is followed using [E]-1-pyrrolidino-1,2-diphenylethene as a starting material. A 2.9-g portion of [E]-1,2-diphenylethene is prepared indicating a yield of 80 percent. The stereochemical purity is found to be greater than 99 percent by $^1$H NMR spectroscopy.

Similar results are obtained starting from [E]-1-morpholino-1,2-diphenylethene.

Examples 1-3 demonstrate the high yield of [E] isomers obtained using the process of this invention.

What is claimed is:

1. A process for preparing an [E] isomer of an alkene comprising three essential steps of
   (1) reacting an enamine wherein the enamine has an alkene portion corresponding to an alkene selected from the group consisting of $C_{3-100}$ linear alkenes and $C_{12-100}$ cyclic alkenes with a hydroborating agent under reaction conditions sufficient to form an intermediate organoborane;
   (2) reacting the organoborane formed in step (1) with an esterifying agent under reaction conditions sufficient to form a boronic ester; and
   (3) oxidizing the boronic ester formed in step (2) in the presence of hydrogen peroxide and in the absence of added base under reaction conditions sufficient to form the [E] isomer of the alkene corresponding to the alkenyl portion of the enamine starting material.

2. The process of claim 1 wherein the hydroborating agent is selected from the group comprising borane.dimethyl sulfide, borane.1,4-oxathiane, borane.tetrahydrofuran and diborane in lower-dialkyl ether.

3. The process of claim 2 wherein the hydroborating agent is borane.dimethyl sulfide.

4. The process of claim 1 wherein the ratio of enamine to hydroborating agent is at least about 1.0:1.0 and no greater than about 2.0:1.0.

5. The process of claim 4 wherein the ratio of enamine to hydroborating agent is at least about 1.0:1.1 and no greater than about 1.1:1.0.

6. The process of claim 1 wherein the hydroborating step is conducted in the presence of a solvent.

7. The process of claim 6 wherein the solvent is tetrahydrofuran.

8. The process of claim 1 wherein the esterification agent is selected from the group consisting essentially of lower alkanols and lower alkyl diols.

9. The process of claim 8 wherein the esterification agent is selected from the group consisting of methanol, ethanol, propanol, ethylene glycol and 1,3-propanediol.

10. The process of claim 9 wherein the esterification agent is methanol.

11. The process of claim 1 wherein the [E] isomer of the alkene is formed in a yield of at least about 70 percent based on the starting enamine.

* * * * *